United States Patent [19]

Rudnick et al.

[11] Patent Number: 5,286,396
[45] Date of Patent: Feb. 15, 1994

[54] NOVEL ALKYLATED PHENOXATHIN BASE STOCK FOR LUBRICANTS

[75] Inventors: Leslie R. Rudnick, Lawrenceville; Carleton N. Rowe, Wenonah, both of N.J.; Derek A. Law, Yardley, Pa.; G. Ali Naghipur, Edmonton, Canada

[73] Assignee: Mobil Oil Corporation, Fairfax, Va.

[21] Appl. No.: 895,500

[22] Filed: Jun. 8, 1992

Related U.S. Application Data

[63] Continuation-in-part of Ser. No. 686,452, Apr. 17, 1991, abandoned.

[51] Int. Cl.$^5$ ................ C10M 135/36; C07D 327/06
[52] U.S. Cl. .................... 252/48.2; 252/46.6; 252/47; 252/47.5; 252/46.7; 549/16
[58] Field of Search ............... 252/48.2, 47.5, 47, 252/46.6, 46.7; 549/16, 5

[56] References Cited

U.S. PATENT DOCUMENTS

| | | | |
|---|---|---|---|
| 2,049,725 | 8/1936 | Smith | 252/48.2 |
| 2,221,819 | 11/1940 | Smith et al. | 549/16 |
| 2,277,833 | 3/1942 | Smith et al. | 549/16 |
| 2,282,686 | 5/1942 | Van Ess | 252/48.2 |
| 4,891,448 | 1/1990 | Garces et al. | 585/453 |
| 5,171,915 | 12/1992 | Forbus et al. | 585/455 |

Primary Examiner—Jacqueline V. Howard
Assistant Examiner—Alan D. Diamond
Attorney, Agent, or Firm—Alexander J. McKillop; Malcolm D. Keen; Howard M. Flournoy

[57] ABSTRACT

Monoalkylated phenoxathins are high-temperature stable lubricant fluids having extreme pressure and antiwear properties, additive solubility and inherent EP-/antiwear properties. These novel phenoxathin fluids may also be used as additives in other lubricant fluids and are prepared by alkylating a phenoxathin in the presence of an acidic zeolite catalyst.

5 Claims, 1 Drawing Sheet

NOVEL ALKYLATED PHENOXATHIN BASE STOCK FOR LUBRICANTS

CROSS REFERENCE TO RELATED APPLICATIONS

This application is a continuation-in-part of copending application Ser. No. 07/686,452, filed Apr. 17, 1991 now abandoned.

BACKGROUND OF THE INVENTION

1. Field of the Invention

This invention is directed to improved lubricant compositions comprising alkylated phenoxathin compounds alone as functionalized lubricant fluids or in combination with synthetic or mineral oil fluids, and to mineral or synthetic lubricant compositions containing said alkylated phenoxathin compounds as additives thereto.

2. Description of Related Art

Linear polyphenyl ether-thioethers and polyphenyl thioethers are known and have been used as lubricants in special applications. These materials suffer from very high cost due to difficult synthesis.

Polyphenyl ethers are known for their high temperature properties as noted in D. Klamen's "Lubricants and Related Products," Verlag Chemie, 1984, pp. 116–121, and references contained therein, and in product bulletin for OS-124 polyphenyl ether by Monsanto.

Mixed polyphenyl ether-thioethers are also known as noted in Monsanto bulletin for MCS-293. Phenoxathin is a heterocyclic aromatic structure which contains the ether oxygen structure found in diphenyl ether and the sulfur structure of thioethers. Phenoxathin, however, is a solid at temperatures up to 56° C. and, therefore, does not possess physical properties attractive for lubricating fluids. Van Ess, U.S. Pat. No. 2,282,686 is directed to the use of certain "thioxins" such as phenoxathin as additives for hydrocarbon oils which are normally susceptible to oxidative deterioration. They are prepared in the presence of aluminum. These substances are added to lube oils, for example, in amount up to 10 wt%.

Smith, et al., U.S. Pat. No. 2,221,819, is directed to a method of making phenothioxine compounds and Smith et al., U.S. Pat. No. 2,277,833 is directed to higher alkyl substituted phenothioxins as novel compounds useful in plastic compositions. They are perpared in the presence of saturated bleaching earth catalyst.

Garces, U.S. Pat. No. 4,891,448 discloses the alkylation of polycyclic aromatics over natural zeolites such as mordenite, offretite and gmelinite.

None of the above noted prior art discloses the method of manufacture and use of alkylated phenoxathins as lubricant basestocks.

The present invention is directed to the alkylation of phenoxathins over zeolite catalysts which surprisingly results in a product which is predominantly or almost completely monoalkylated. Synthesized catalysts are preferred. Monoalkylated product comprises up to at least about 90% of the alkylation product in accordance with the present invention. In some instances the monoalkylation rate approaches 100%.

To the best of applicants' knowledge and belief the herein described alkylated phenoxathins have not been used previously as functional lubricant fluids or additives therefor.

BRIEF SUMMARY OF THE INVENTION

This invention is directed to novel alkylated phenoxathin compounds having high-temperature stability, excellent additive solubility characteristics and inherent EP/antiwear properties.

Incorporation of linear alkyl hydrocarbon groups into phenoxathins eliminates the high costs involved in the preparation of polythioether synthesis and converts phenoxathin, which is solid at room temperature, to a novel, relatively inexpensive lubricant having excellent extreme pressure and antiwear properties. The use of these adducts as a lubricant or lubricant additive in either mineral or synthetic lubricants is unique and provides improved properties and performance benefits due to inherent synergism. It is expected that the performance benefits will include antifatigue, antispalling, antistaining, antisquawking, improved additive solubility, improved load carrying/bearing, extreme pressure, improved theremal and oxidative stability, friction reducing, antiwear, anticorrosion, cleanliness improving, low- and high-temperature antioxidant, demulsifying, emulsifying and detergency properties.

It is therefore an object of this invention to provide novel and improved lubricant compositions comprising the phenoxathin compounds in accordance with the invention and novel lubricant compositions containing minor proportions of said alkylated phenoxathin compounds as additives. Additionally, the fluids may function as carriers for fuel additives or as fuel cleaniness, detergent, etc. fuel additives.

DESCRIPTION OF THE PREFERRED EMBODIMENTS

Figure 1:
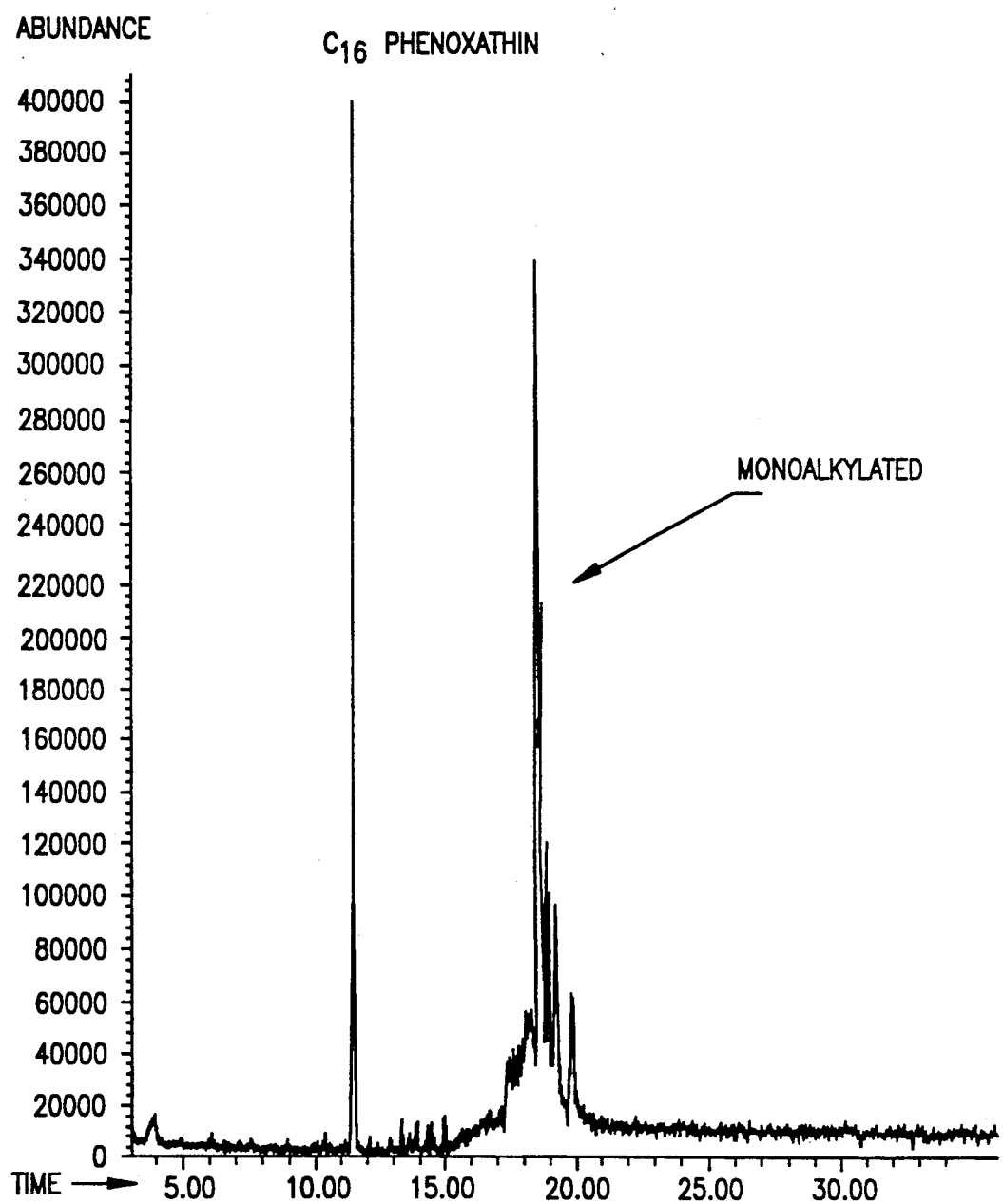
FIG. 1 is a GCMS (gas chromatography mass spectrometry) graph of product in accordance with the invention.

Broadly, the novel class of hydrocarbon products of the present invention can be characterized as hydrocarbyl adducts of phenoxathin.

The products obtained from the reaction of a linear olefin and phenoxathin in the presence of zeolite catalysts are unique not only in composition and structure but in utility. Part of the uniqueness is derived from the reaction over zeolite catalysts; generally, they have a higher VI at a given viscosity. The incorporation of various alkyl groups into the phenoxathin structure provides compositions of different viscosities and low-temperature properties.

Thermal stability of these alkylated phenoxathins is excellent and believed improved over materials of branched structure due to the facility for carbon-carbon bond breaking in the latter materials.

These unique lubricants exhibit beneficial properties from the unique reaction of olefin with the phenoxathin structure in such a way as to produce a high proportion of linear groups. This is a direct result of the catalytic reaction. This combination provides for the novel structural class disclosed herein. The use of these compositions of matter as either functionalized alkylated phenoxathin lubricant fluids or lubricant additives is believed to be novel.

Although a high porportion of linear hydrocarbyl groups are believed to be most preferred, mixtures of linear and more branched or cyclic hydrocarbyl groups can provide benefical properties. In some circumstances, linear groups may be preferred, in others more branched and/or cyclic groups may be preferred. For example, some of the cyclics can actually improve some properties, such as traction.

The hydrocarbyl alkylating agent can contain from $C_3$ to $C_{500}$, preferably $C_6$–$C_{50}$ and most preferably $C_8$ to $C_{18}$. The hydrocarbyl group of the alkylating agent can optionally contain one or more S, N, 0, P and/or F or mixtures thereof. The hydrocarbyl group can be alkyl, alkenyl, alkynyl, arylalkyl, alkylaryl, aryl, aliphatic, cyclic, linear or branched. The preferred alkyating agents are olefins, especially 1-olefins.

Phenoxathin has been prepared as described in Organic Synthesis, Collective Vol. II, p. 485.

The preparation of the novel compositions in accordance with the invention may be by means of a thermal or catalytic addition reaction. The exact mechanism of the reaction is not important to the purposes of this invention, so long as the hydrocarbyl group becomes attached to the phenoxathin compounds described herein in the presence of a zeolite catalyst.

Generally, the method of reaction between the hydrocarbyl alkylating agent and the phenoxathin is the combination of these reactants in the presence of zeolite catalysts. More particularly, in one preferred method, the alkylated phenoxathin lubricant fluids comprising a substantially monoalkylated phenoxathin are produced by alkylating the phenoxathin with a suitable alkylating agent in the presence of an acidic zeolite catalyst. This reaction is affected at temperatures ranging from ambient to about 350° C., preferably from 100°–250° C. and most preferably from 180°–240° C. over a period required to produce the desired conversion of reactants to product. Optionally, the reaction can be performed in a batch or semi-batch mode by continuous or partial addition of catalyst or hydrocarbyl substituent to the phenoxathin.

The catalyst can be used at levels ranging from 1 gram/mole of aromatic to 100 grams/mole of aromatic, preferably from 5 g/mole of aromatic to 50 grams/mole of aromatic, and most preferably from 10–30 grams catalyst/mole of aromatic. The catalyst may be steamed, calcined or fresh. Generally speaking the molar ratio of hydrocarbyl substituent to the phenoxathin varies from about 0.5:1.0 to about 10.0:1.0 and preferably from about 1.0:10 to about 4.0:100. Catalysts which can be used include zeolites X, Y, UHP-Y, ZSM-20, zeolite beta and MCM-22.

The above preferred method demonstrates the use of the catalysts of choice. MCM-22 is disclosed in U.S. Pat. No. 4,954,325 which is incorporatd herein in its entirety by reference. It is also described in U.S. Pat. No. 5,100,534, which is incorporated herein in its entirety by reference, as a crystalline aluminosilicate zeolite. MCM-22 is also described in U.S. Pat. No. 5,103,066 as having a CI (constraint index) of 1.5 at 454° C. U.S. Pat. No. 5,103,066 is incorporated herein by reference.

Constraint Index (CI) values for some typical zeolites are given below.

|  | CI (at test temperature) |
| --- | --- |
| ZSM-5 | 6–8.3 (371° C.–316° C.) |
| ZSM-22 | 7.3 (427° C.) |
| MCM-22 | 1.5 (454° C.) |
| Dealuminized Y | 0.5 (510° C.) |

The method by which Constraint Index of acidic zeolites is determined is described fully in U.S. Pat. No. 4,016,218 incorporated herein by reference for details of the method. The above-described CI is a highly important definition of the zeolites which are useful in the process of the present invention.

The alpha value is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 $\sec^{-1}$). The alpha test is described in U.S. Pat. No. 3,354,078 and in *J. Catalysis*, 4, 527 (1965); 6, 278 (1966); and 61, 395 (1980), to which reference is made for a description of the test. The experimental conditions of the test used to determine the alpha values referred to in this specification include a constant temperature of 538° C. and a variable flow rate as described in detail in *J. Catalysis*, 61, 395 (1980).

FCC (fluid catalytic cracking) catalysts based on ultrastable Y type (USY) zeolites are well known in the art to make gasoline having a higher octane number than FCC catalysts based on rare earth exchanged Y (REY) or calcined rare earth exchanged Y (CREY); see U.S. Pat. No. 5,102,530 which is incorporated herein by reference. It is further disclosed in U.S. publication/notice H 449 (Mar. 1, 1988) to Rudesill that the commercially available FCC cracking catalyst (Octacat) comprises about 40% Ultrastable Type Y zeolite combined with a silica-alumina sol binder and kaolin matrix and that preferably the USY containing Octacat may comprise from about 15 to about 60 wt. % USY and more preferably from about 35 to about 45 wt. % USY. H 449, filed Jul. 3, 1987 and published Mar. 1, 1988 to Rudesill is incorporated herein by reference.

The monoalkylated products obtained with the zeolite catalysts exhibit superior properties in comparison to the alkylated phenoxathins prepared by reaction of the alkylating agent in the presence of $AlCl_3$ and other proton, and Lewis acids as described in G. A. Olah's "Friedel-Crafts and Related Reactions", Vol, I, 1963, Interscience Publishers.

As noted hereinabove the novel products in accordance with the invention are substantially, i.e., up to 100% and at least about 95% monoalkylated. FIG. 1 which is a GCMS graph of alkylated product in accordance with the invention corroborates this. In the Figure, a measure of abundance is the quantitative amount of material and time is the running time in minutes. The spike which occurs at about 11½ minutes is unreacted material. Substantially all (approaching or about 100%) of the reacted material was monoalkylated.

The hydrocarbon compositions of the present invention relate to improved thermally and oxidatively stable fluids. These may be used optionally as liquid lubricants or as additives in liquid lubricant compositions, and as solid lubricants or in solid lubricant compositions including greases, such a polyurea, lithium carboxylate or clay-thickened greases.

These hydrocarbon compositions may also be used in combination with prior art additives, for example, antioxidants, EP/antiwear agents, inhibitors, detergents and dispersants, and viscosity index improvers. Non-limiting examples of antioxidants include phenols which can be hindered and aromatic amines.

Non-limiting examples of EP/antiwear additives include zinc phosphorodithioates, sulfurized esters, sulfurized olefins, phosphonates, phosphites, phosphorothionates, etc. Non-limiting examples of inhibitors include DMTD, phenothiazine, etc. Non-limiting examples of detergents and dispersants include sulfonates, phenates, and polymeric succinimides. These can be either metallic or non-metallic. Metallic detergents can be calcium or magnesium derived and can be neutral or over based.

The hydrocarbon compositions of this invention can be used alone or in combination with other synthetic and/or mineral oil fluids.

When the alkylated phenoxathins are used as the base fluid or feedstock they will generally have a viscosity range varying from about 3 to about 20 cSt at 100° C. with a preferred range of 3.5 to 10.

The fluids in accordance with the invention have been found to be highly useful when combined or blended with synthetic or mineral based fluids and particularly with ester-containing fluids such as synthetic polyalphaolefins (PAO). Any suitable blending ratio may be used, for example, a blend of 20% alkylated phenoxathin (AP) and 80% PAO has been found to be very advantageous. However, the AP may constitute a majority of the blends up to about 80–100% or less than 100%. It is noted that AP fluids may be used as replacements for or as components of current commercial lubricant formulations.

When the compositions of the present invention are used in combination with other synthetic and/or mineral oil fluids, the below described oils of lubricating viscosity may be used. In general, mineral oils, both paraffinic, naphthenic and mixtures thereof, employed as the lubricant, or grease vehicle, may be of any suitable lubricating viscosity range, as for example, from about 1.0 cSt at 100° F. to about 1000 cSt at 100° F., and preferably, from about 2.0 to about 60 cSt at 100° F. The preferred oils may have viscosity indexes ranging to about 150. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials.

In general, grease thickeners may be employed which do not melt and dissolve when used at the required temperature within a particular environment; however, in all other respects, any materials which is normally employed for thickening or gelling hydrocarbon fluids for foaming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes land silicones (polysiloxanes) and alkyl-substituted diphenyl ethers.

When used as additives the materials in accordance with the invention have the ability to improve both the thermal and oxidative stability as well as the additive solubility of the oleagenous materials, i.e., synthetic and/or mineral oil fluids with which they have been blended.

It is to be understood, however, that the prior art additives disclosed herein are used for their known purposes do not detract from the value of the compositions of this invention, rather these materials enhance the beneficial characteristics of the disclosed alkylated phenoxathin fluids.

Lubricant compositions in accordance with the invention may comprise from less than about 1 to about 100% of the alkylated phenoxathins of the invention and/or from less than about 100% to about 1% of a synthetic or mineral oil of lubricating viscosity or grease prepared therefrom and from about 0.001 to about 20 wt% of additive material based on the total weight of the composition.

The following examples are exemplary only and are not intended to limit the invention.

EXAMPLE 1

To a vigorously stirred mixture of phenoxathin (202 g, 1.0 mole) and 1-tetradecene (196 g, 1.0 mole) in a flask fitted with thermocouple and reflux condenser was added 19.5 g of FCC Octacat USY catalyst. The mixture was heated to 200° C. with stirring for six hours. After cooling to room temperature, the mixture was filtered to remove catalyst and vacuum distilled to 170° C. at 0.5–1.5 mmHg to remove unreacted starting materials.

EXAMPLE 2

Using the procedure in Example 1, phenoxathin (202 g, 1.0 mole) and 1-tetradecene (196 g, 1.0 mole) were reacted using 39 grams of FCC Octacat USY catalyst.

EXAMPLE 3

Using the procedure in Example 1, phenoxathin (202 g, 1.0 mole) and 1-hexadecene (224.43 g, 1.0 moles) were reacted using 42.4 grams of FCC Octacat USY catalyst.

EXAMPLE 4

To a stirred mixture of 1-octene, 224.2 g (2 moles), and phenoxathin (202 g, 1 mole), was added 2.0 grams of anhydrous $AlCl_3$, and heated at reflux for six hours. The mixture was cooled, washed to remove inorganic materials, dried over anhydrous $MgSO_4$. Gas chromatographic analysis showed essentially complete reaction of starting material. Color of this material was >5 whereas the product of Example 1 was <2.0.

Typical properties of exemplary hydrocarbyl phenoxathins are shown in Table 1, below.

TABLE 1

| Hydrocarbyl | $C_{14}$ | $C_{16}$ | $C_{18}$ |
| --- | --- | --- | --- |
| KV @ 100° C., cSt | 7.8 | 7.93 | 9.13 |

TABLE 1-continued

| VI | 41.4 | 61.6 | 75.2 |
|---|---|---|---|
| Pour Point (°C.) | −35 | −35 | −30 |

EVALUATION OF PRODUCTS

Performance as a Lubricant Having Improved Antiwear

Hexadecene alkylated phenoxathin was compared to a polyolefin base stock in a Four-Ball Wear test. The results show that at higher load, the alkyl phenoxathin produced less wear than the other base stock, without any adverse effect on coefficient of friction (f).

The antiwear properties of the examples were evaluated using the Four Ball Wear Test as shown in Table 2. The results clearly exhibit the excellent antiwear properties inherent in these unique compositions.

In the Four Ball Test three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 5200 steel for thirty minutes under 40 kg load at 1800 rpm and 200° F. If additional information is desired consult test method ASTM D2266 and/or U.S. Pat. No. 4,761,482.

TABLE 2

FOUR-BALL WEAR TEST RESULTS
(200° F./40 Kg/30 min)

| | 1800 RPM | |
|---|---|---|
| | WSD, mm | f |
| $C_{16}$ Phenoxathin | 0.617 | 0.094 |
| polyolefin base stock | 1.66 | 0.076 |

The Four-Ball Wear Test results as noted above clearly demonstrate the excellent antiwear properties of these compositions/fluids.

PERFORMANCE AS A LUBRICANT WITH IMPROVED LOAD CARRYING PROPERTIES

Load-carrying properties were measured using ASTM D2596 at both room temperature and 100° C.

| | 23° C. | | | 100° C. | | |
|---|---|---|---|---|---|---|
| | LNS | LWI | Weld | LNS | LWI | Weld |
| Polyolefin base stock | 50 | 22.7 | 126 | 32 | 14.6 | 126 |
| $C_{16}$ Phenoxathin | 50 | 23.7 | 160 | 40 | 20.6 | 160 |

IMPROVED THERMAL STABILITY OF ALKYL PHENOXATHIN OVER OTHER LUBRICANT CLASSES

The results of thermal stability tests are shown below:

| | Thermal Stability Test |
|---|---|
| Sample | % Viscosity Change After 72 hrs at 288° C. |
| $C_{16}$-Phenoxathin | −15 (at 310° C.) |
| CSL* (Sample 1) | −14.8 |
| CSL (Sample 2) | −19.4 |
| CSL (Sample 3) | −38.8 |
| CSL (Sample 4) | −60.9 |
| CSL (Sample 5) | −67.9 |
| Lube Ester (polyol) | −34.2 |

*Commercial Synthetic Lubricant

The use of alkylated phenoxathin as a suitable replacement for components of current lubricant formulations is highly desirable. For example, synthetic and/or mineral based lubricant composition containing esters for improved additive solubility would be significantly improved by replacement with alkylated phenoxathin due to its excellent additive solubility and EP/antiwear properties. Alkylated phenoxathins prepared as described herein provide excellent base stock properties and could themselves serve as the base stock in formulations for various applications, for example, applications where high temperatures and EP are maintained. Fuel compositions are also comtemplated for use herein, these include both hydrocarbon fuels, including gasoline, naphtha and diesel fuels or alcoholic fuels or mixtures of alcoholic and hydrocarbon fuels. Fuel compositions can contain 10 to 1,000 pounds of additive per 1000 barrels of fuel or more preferably 25 to 250 pounds per 1000 barrels of fuel.

Although the present invention has been described with preferred embodiments, it is to be understood that modifications and variations may be resorted to, without departing from the spirit and scope of this invention, as those skilled in the art will readily understand. Such variations and modifications are considered within the purview and scope of the appended claims.

What is claimed is:

1. A process for the preparation of a high-temperature stable lubricant fluid or lubricant additive comprising reacting in the presence of an acidic zeolite catalyst selected from the group consisting of zeolites X, Y, UHP-Y, ZSM-20, zeolite beta and MCM-22, (1) a hydrocarbyl alkylating agent selected from alpha olefins containing from 3 to about 500 carbons and optionally containing S, N, O, P, F, or mixtures thereof, and (2) a phenoxathin wherein the reaction temperature varies from ambient to about 350° C., the molar ratio of hydrocarbyl alkylating agent to phenoxathin varies from 0.5:1.0 to about 10.1:1.0 and the amount of catalyst varies from 5 to about 100 grams of catalyst to about 1 mole of phenoxathin and wherein the reaction product comprises a monosubstituted adduct.

2. The process of claim 1 wherein the alkylating agent is a $C_8$ to $C_{18}$ alpha-olefin.

3. The process of claim 1 wherein the catalyst is an ultrastable Y zeolite catalyst.

4. The process of claim 1 wherein the reactants are 1-tetradecene and phenoxathin and the catalyst is an ultrastable Y zeolite catalyst.

5. The process of claim 2 wherein the reactants are 1-hexadecene and phenoxathin and the catalyst is an ultrastable Y zeolite catalyst.

* * * * *